United States Patent [19]

Cesa et al.

[11] Patent Number: 5,041,659

[45] Date of Patent: Aug. 20, 1991

[54] SYNTHESIS OF N-DISUBSTITUTED AMIDES BY REACTION OF AMIDES WITH CERTAIN ORGANIC HYDROXYL COMPOUNDS

[75] Inventors: Mark C. Cesa, South Euclid; Sandra L. Denman, Brunswick, both of Ohio

[73] Assignee: The Standard Oil Company, Cleveland, Ohio

[21] Appl. No.: 515,148

[22] Filed: Apr. 26, 1990

[51] Int. Cl.$^5$ .......................................... C07C 233/05
[52] U.S. Cl. ..................... 564/157; 564/160; 564/215; 564/224
[58] Field of Search ............. 564/215, 197, 199, 203, 564/201, 224, 160, 157

[56] References Cited

U.S. PATENT DOCUMENTS 4,853,485  8/1989  Bellis ................................. 564/215

FOREIGN PATENT DOCUMENTS 4828417   3/1970  Japan .
62-201854 4/1987  Japan .
789533    8/1983  United Kingdom .

OTHER PUBLICATIONS

Geivandor, *Zh Org Khim* 1983, 19, 738–739.
Kashiwagi et al, *Nippon Kagako Kaishi*, 1980, pp. 279–281.
Cheesman et al., *J Chem Soc*, 1962, 5277–5280.
Watanabe et al, *Bull. Chem. Soc. Japan*, 1983, 56, 2647–2651.

*Primary Examiner*—Richard L. Raymond
*Assistant Examiner*—Brian Bembenick
*Attorney, Agent, or Firm*—C. S. Lynch; D. J. Untener; L. W. Evans

[57] ABSTRACT

Disclosed is a method which comprises introducing into a reaction zone a feed which comprises a hydroxyl compound reactant, R"OH, at least one amide reactant selected from R-CONH$_2$ and R-CONHR', and an inorganic catalyst, thereby reacting R"OH with said amide reactant to produce a rection mixture containing at least one disubstituted amide selected from R-CONHR"$_2$ and R-CONHR'R", wherein each of R, R' and R" contains no acetylenic unsaturation and 1 to 30 carbon atoms, each of R, R' and R" is selected from a hydrocarbyl group and a hydrocarbyl group that is substituted with a group selected from carbamoyl, hydrocarbylcarbamoyl, dihydrocarbylcarbamoyl, and hydroxyl, wherein said inorganic catalyst is selected from phosphates and sulfates of a Group 13 element and of a Group 2 metal having an atomic weight less than 145, and mixtures thereof.

6 Claims, No Drawings

SYNTHESIS OF N-DISUBSTITUTED AMIDES BY REACTION OF AMIDES WITH CERTAIN ORGANIC HYDROXYL COMPOUNDS

This invention relates to the synthesis of N-disubstituted amides by reaction of amides with certain organic hydroxyl compounds using inorganic acids as catalysts for such reaction.

The important industrial solvent, N,N-dimethylacetamide, is currently prepared industrially from acetic acid and dimethylamine. It is a superior organic solvent, with high boiling range and good thermal stability relative to other amides such as dimethylformamide. The current DMAC synthesis suffers from relatively high raw material costs. As a result, DMAC has a high price (about $1.00 per pound). This high price precludes use of DMAC in many applications where relatively inferior but lower priced solvents are used.

The process of the present invention has the potential to lower N-disubstituted amides production costs substantially because of the much lower prices of the starting materials compared with the price of the raw materials of the current synthetic method, thus offering the potential for growth of DMAC demand into applications where its superior properties would be an advantage.

It is an object of the present invention to improve the process of making N-disubstituted amides.

It is a further object of the invention to lower the cost of making N-disubstituted amides by condensing amides with alcohols in the presence of certain inorganic catalysts.

Other objects, as well as aspects and advantages, of the invention will become apparent from a study of the specification, including the specific examples and the claims.

The foregoing and other objects are realized by the present invention according to which there is provided a method which comprises introducing into a reaction zone a feed which comprises a hydroxyl compound reactant, R"OH, at least one amide reactant selected from R—$CONH_2$ and R—CONHR', and an inorganic catalyst thereby reacting R"OH with said amide reactant to produce a reaction mixture containing at least one disubstituted amide selected from R—$CONR"_2$ and R—CONR'R", wherein each of R, R' and R" contains no acetylenic unsaturation and 1 to 30 carbon atoms, each of R, R' and R" is selected from a hydrocarbyl group and a hydrocarbyl group that is substituted with a group selected from carbamoyl, hydrocarbylcarbamoyl, dihydrocarbylcarbamoyl, and hydroxyl, wherein said inorganic catalyst is selected from phosphates and sulfates of a Group 13 element and of a Group 2 metal having an atomic weight less than 145, and mixtures thereof.

The Groups refer to the Periodic Table of the Elements that numbers the groups from 1 to 18, appearing in Chemical and Engineering News, 63, (5), 27, 1985.

A variety of acidic catalysts has been reported for N-alkylation of amides with alcohols. $H_2SO_4$ is an effective catalyst for condensation of tertiary alcohols (e.g. tert-butyl alcohol) with amides (R. Kh. Geivandov, *Zh. Org. Khim.*, 1983, 19, 738-739; M. T. Harvey, S. Caplan, U.S. Pat. No. 2,461,509). Organic acids (G. W. H. Cheeseman, R. C. Poller, *J. Chem. Soc.*, 1962, 5277-5280), ammonium salts (H. Kashiwagi, S. Enomoto, *Nippon Kagaku Kaishi*, 1980, 279-281), and zeolites (JP 62 201,854 [Mitsubishi Chem. Ind.]) have also been reported. Particularly effective catalysts for primary alcohols are transition metal salts. For example, oxides, peroxides, sulfides, oxyhalogenates, hydroxides, inorganic salts, or organic salts of copper, silver, gold, zinc, cadmium, mercury, titanium, zirconium, tin, lead, chromium, molybdenum, tungsten, iron, cobalt, nickel, rhodium, palladium, iridium, platinum, or thorium are reported in a patent to Asahi Chemical Industry Co. (S. Senoo, Y. Fukuoka, K. Sasaki, JP 48 28,417); and phosphine-coordinated ruthenium halides are also effective (Y. Watanabe, T. Ohta, Y. Tsuji, *Bull. Chem. Soc. Japan*, 1983, 56, 2647-2651.) The alkylation of amides with alcohols may also be carried out in the absence of catalyst (A. Wolfram, E. Schallus, GB 789,533).

According to the present invention, the catalyzed alkylation of amides with alcohols of the present invention can be carried out in either the vapor phase or in the liquid phase, at atmospheric pressure or reduced or elevated pressure, in a batch mode, flow mode, or continuous stirred reactor mode.

The presence of inert diluents for any of the starting materials is within the scope of the invention. For example, the use of nitrogen or other inert gas in the reaction zone is permitted, and is favored in high-temperature liquid phase conditions to minimize unwanted side reactions. Also, the use of inert solvents with the reactants such as, for example (but not restricted to), alkanes and aromatic hydrocarbons is within the scope of the invention.

The reactants can be employed from the beginning of the reaction in the full amounts required for the reaction, or the reactants can be introduced to the reaction zone successively or stepwise during the course of the reaction.

The catalysts can be unsupported or supported on organic polymers or inorganic oxide supports if desired.

Optimum catalyst amounts can be determined by routine experiments, but often vary from 0.0001 to 10 moles introduced into the reaction zone per 100 moles of the amide reactant(s) introduced into the reaction zone. More usually the amount is from 0.01 to 5 moles per 100 moles of the amide reactant(s) introduced into the reaction zone.

The process of this invention can be carried out at from 20° to 600° C. Preferred temperatures range from 100° C. to 500° C.; at lower temperatures the reaction rate is unsuitably low, and at higher temperatures undue amounts of byproducts are formed.

Pressures can range from 0.1 atmosphere to 200 atmospheres or more. In liquid phase runs carried out in pressure vessels with low-boiling reactants, high reaction temperatures required for sufficient reaction rates result in pressures well above 1 atmosphere.

The alcohol/amide starting materials mole ratio can range from 0.1 to 20, but usual ratios range from 1.0 to 10. Lower amounts of alcohol relative to amide result in reduced amide conversion and product yields, and higher amounts can alcoholyze amide products, lowering yield of desired product.

The following examples of the invention are exemplary and should not be taken as in any way limiting.

EXAMPLE 1

A mixture of N-methylacetamide (36.82 g, 0.504 mol), methanol (17.85 g, 0.5578 mol), and $BPO_4$ (5.32 g, 0.0503 mol) was placed in a stainless steel autoclave of 300 ml internal volume. The reactor was sealed, and the reaction mixture was purged with nitrogen through a dip tube for 30 minutes. The reactor was then heated to 240° C., and the reaction mixture was stirred vigorously. The temperature of the reaction mixture reached 240° C., and the reaction mixture was stirred at that temperature for 3.5 hours. The reactor was then cooled, and the reaction mixture was analyzed by gas chromatography. Conversion of methanol was 86% and conversion of N-methylacetamide was 46%. The yield of N,N-dimethylacetamide was 6.9%, corresponding to a selectivity of 15.1%.

EXAMPLE 2

A mixture of acetamide (29.42 g, 0.498 mol), methanol (84.4 g, 2.64 mol), and $BPO_4$ (6.01 g, 0.057 mol) was placed in a stainless steel autoclave of 300 ml internal volume. The reactor was sealed, and the reaction mixture was purged with nitrogen through a dip tube for 30 minutes. The reactor was then heated to 330° C., and the reaction mixture was stirred vigorously. The temperature of the reaction mixture reached 240° C., and the reaction mixture was stirred at that temperature for 2 hours. The reactor was then cooled, and the reaction mixture was analyzed by gas chromatography. Conversion of methanol was 58.3% and conversion of acetamide was 78.7%. The yield of N,N-dimethylacetamide was 3.0%, corresponding to a selectivity of 3.8%, and the yield of N-methylacetamide was 62.2%, corresponding to a selectivity of 79.1%.

EXAMPLE 3

A mixture of N-methylacetamide (36.57 g, 0.5003 mol), methanol (32.05 g, 1.0002 mol), and $BPO_4$ (1.5970 g, 0.0151 mol) was placed in a stainless steel autoclave of 300 ml internal volume. The reactor was sealed, and the reaction mixture was purged with nitrogen through a dip tube for 30 minutes. The reactor was then heated to 362° C., and the reaction mixture was stirred at that temperature for 5 hours. The reactor was then cooled, and the reaction mixture was analyzed by gas chromatography. Conversion of methanol was 80.9% and conversion of N-methylacetamide was 90.2%. The yield of N,N-dimethylacetamide was 40.1%, corresponding to a selectivity of 44.4%, both better than the same reaction without a catalyst, as shown in Example A that follows:

COMPARATIVE EXAMPLE A

A mixture of N-methylacetamide (36.57 g, 0.5003 mol) and methanol (32.05 g, 1.0002 mol) was placed in a stainless steel autoclave of 300 ml internal volume. No catalyst was added. The reactor was sealed, and the reaction mixture was purged with nitrogen through a dip tube for 30 minutes. The reactor was then heated to 362° C., and the reaction mixture was stirred at that temperature for 5 hours. The reactor was then cooled, and the reaction mixture was analyzed by gas chromatography. Conversion of methanol was 81.0% and conversion of N-methylacetamide was 85.9%. The yield of N,N-dimethylacetamide was 36.1%, corresponding to a selectivity of 42.0%.

EXAMPLE 4

A mixture of acetamide (29.60 g, 0.5011 mol), methanol (32.06 g, 1.0006 mol), and $BPO_4$ (1.59 g, 0.0150 mol) was placed in a stainless steel autoclave of 300 ml internal volume. The reactor was sealed, and the reaction mixture was purged with nitrogen through a dip tube for 30 minutes. The reactor was then heated to 362° C., and the reaction mixture was stirred at that temperature for 4 hours. The reactor was then cooled, and the reaction mixture was analyzed by gas chromatography. Conversion of methanol was 89.5% and conversion of acetamide was 93.0%. The yield of N,N-dimethylacetamide was 42.6%, corresponding to a selectivity of 45.8%, and the yield of N-methylacetamide was 30.3%, corresponding to a selectivity of 32.6%. Conversion of acetamide, and yield and selectivity are better than Comparative Example B.

COMPARATIVE EXAMPLE B

A mixture of acetamide (29.54 g, 0.5001 mol) and methanol (32.05 g, 1.0002 mol) was placed in a stainless steel autoclave of 300 ml internal volume. The reactor was sealed, and the reaction mixture was purged with nitrogen through a dip tube for 30 minutes. The reactor was then heated to 363° C., and the reaction mixture was stirred vigorously at that temperature for 4 hours. The reactor was then cooled, and the reaction mixture was analyzed by gas chromatography. Conversion of acetamide was 83.3%. The yield of N,N-dimethylacetamide was 31.7%, corresponding to a selectivity of 38.1%, and the yield of N-methylacetamide was 30.8%, corresponding to a selectivity of 37.0%.

EXAMPLE 5

A stainless tubular steel upward flow microreactor was charged with $BPO_4$ (ground to 20/40 mesh, 3 mL) and immersed in a molten salt bath at 250° C. While $N_2$ was fed through the reactor at a flow rate of 16.4 mL/min (measured at room temperature and atmospheric pressure), a 4.9/1 molar mixture of methanol and N-methylacetamide was fed over the catalyst at a flow rate corresponding to a liquid contact time of 2 sec. The reactor effluent was passed through an ice-cooled scrubber containing water. After 101 mmol of methanol and 20.06 mmol of N-methylacetamide were reacted in the above manner, the contents of the scrubber were analyzed by gas chromatography. Methanol conversion was 10.9% and N-methylacetamide conversion was 60.95%. The yield of N,N-dimethylacetamide was 0.89%, corresponding to a selectivity of 1.46%.

As will be evident to those skilled in the art various modifications of this invention can be made or followed in the light of the foregoing disclosure and discussion without departing from the spirit and scope of the disclosure or from the scope of the claims.

We claim:

1. A method which comprises introducing into a reaction zone a feed which comprises a hydroxyl compound reactant, R"OH, at least one amide reactant selected from $R—CONH_2$ and R—CONHR', and an inorganic catalyst, thereby reacting R"OH with said amide reactant to produce a reaction mixture containing at least one disubstituted amide selected from R—CONR"$_2$ and R—CONR'R", wherein each of R, R' and R" contains no acetylenic unsaturation and 1 to 30 carbon atoms, each of R, R' and R" is a hydrocarbyl group, and wherein said inorganic catalyst is selected from phosphates and sulfates of a Group 13 element and of a Group 2 metal having an atomic weight less than 145, and mixtures thereof.

2. A method according to claim 1 which comprises introducing into a reaction zone methanol, at least one amide selected from acetamide and N-methylacetamide, thereby reacting methanol with said amide to produce a reaction mixture containing N,N-dimethylacetamide.

3. A method of claim 1 wherein the mole ratio of R"OH to said selected amide(s) introduced into the reaction zone is from 0.1 to 20.

4. A method of claim 3 wherein said mole ratio is from 1 to 10.

5. A method of claim 2 wherein the mole ratio of methanol to $CH_3CONHR'$ introduced into the reactions zone is from 0.1 to 20.

6. A method of claim 5 wherein said mole ratio is from 1 to 10.

* * * * *